United States Patent
Chappa

(10) Patent No.: US 7,575,781 B2
(45) Date of Patent: Aug. 18, 2009

(54) METHOD FOR DEPOSITING A POLYMERIC COATING ON A SUBSTRATE

(75) Inventor: Ralph A. Chappa, Prior Lake, MN (US)

(73) Assignee: Sur Modics, Inc., Eden, Prairie, MN (US)

( * ) Notice: Subject to any disclaimer, the term of this patent is extended or adjusted under 35 U.S.C. 154(b) by 575 days.

(21) Appl. No.: 10/911,228

(22) Filed: Aug. 3, 2004

(65) Prior Publication Data

US 2006/0029721 A1    Feb. 9, 2006

(51) Int. Cl.
C23C 16/00 (2006.01)
A61L 33/04 (2006.01)

(52) U.S. Cl. .................... 427/255.6; 427/2.24

(58) Field of Classification Search .............. 427/255.6, 427/2.1, 2.24
See application file for complete search history.

(56) References Cited

U.S. PATENT DOCUMENTS

| | | | |
|---|---|---|---|
| 5,538,758 A | 7/1996 | Beach et al. | |
| 5,670,212 A | 9/1997 | Staring et al. | |
| 5,952,060 A * | 9/1999 | Ravi | 427/577 |
| 5,958,510 A * | 9/1999 | Sivaramakrishnam et al. | 427/255.6 |
| 6,086,952 A | 7/2000 | Lang et al. | |
| 6,165,554 A | 12/2000 | Halpern et al. | |
| 6,179,922 B1 | 1/2001 | Ishikawa et al. | |
| 6,193,811 B1 * | 2/2001 | Sundarrajan et al. | 134/19 |
| 6,281,144 B1 | 8/2001 | Cleary et al. | |
| 6,299,604 B1 * | 10/2001 | Ragheb et al. | 604/265 |
| 6,331,211 B1 | 12/2001 | Xu et al. | |
| 6,358,863 B1 | 3/2002 | Desu et al. | |
| 6,406,544 B1 * | 6/2002 | Stewart | 118/719 |
| 6,495,208 B1 | 12/2002 | Desu et al. | |
| 6,569,107 B2 | 5/2003 | Jalisi et al. | |
| 6,586,048 B2 * | 7/2003 | Welch et al. | 427/255.6 |
| 6,663,713 B1 | 12/2003 | Robles et al. | |
| 6,906,257 B2 * | 6/2005 | Saccomanno et al. | 174/36 |
| 2001/0029888 A1 | 10/2001 | Sundarrajan et al. | |
| 2004/0086636 A1 | 5/2004 | Gregory | |
| 2004/0247274 A1 | 12/2004 | Gregory | |
| 2005/0146267 A1 | 7/2005 | Lee et al. | |

OTHER PUBLICATIONS

Vaeth, Kathleen, et al., "Chemical Vapor Deposition of Thin Polymer Films Used in Polymer-Based Light Emitting Diodes". Advanced Materials, 1997, vol. 9, No. 6, pp. 490-493.*
Bienkiewicz, J., et al., "Plasma-Enhanced Parylene Coating for Medical Device Applications". Medical Device Link, reprinted from Medical Device Technology, Jan./Feb. 2006, no page numbers.*
K. M. Vaeth et al., "Blue Electroluminescent Copolymers by Parylene-Based Chemical Vapor Deposition", *Macromolecules* 2000, 33, No. 18, 5336-5339.

* cited by examiner

*Primary Examiner*—Bret Chen
(74) *Attorney, Agent, or Firm*—Pauly, DeVries Smith & Deffner, L.L.C.

(57) ABSTRACT

The present application relates to a method for vapor depositing a polymeric coating onto a substrate. In an embodiment, the invention is a method for applying a polymer coating to a substrate comprising performing a bake-out cycle with a chemical vapor deposition system and performing a deposition cycle with the chemical vapor deposition system.

31 Claims, 2 Drawing Sheets

METHOD FOR DEPOSITING A POLYMERIC COATING ON A SUBSTRATE

FIELD OF THE INVENTION

The present application relates to a method for depositing a polymeric coating onto a substrate. More specifically, the present application relates to a method for vapor depositing a polymeric coating onto a substrate.

BACKGROUND OF THE INVENTION

Polymeric materials are deposited onto substrates for a wide variety of purposes. By way of example, polymeric materials may be deposited onto the surface of a medical device to impart certain properties to the medical device.

Polymeric materials can be applied in many ways. For example, polymeric materials can be applied through techniques including dip coating, spraying, rolling, etc. Some types of polymeric materials can be applied using a chemical vapor deposition (CVD) process or a plasma deposition process. By way of example, parylene can be deposited onto the surface of a substrate using a vapor deposition process.

Materials that are vapor deposited are typically vaporized with a heat source and then allowed to condense on the surface of a desired substrate. Some polymeric materials applied with vapor deposition are activated after vaporization so they can chemically bond with other polymeric materials or the surface of the substrate.

Adhesion of a polymeric material to the surface of a substrate can be important for proper performance of the end product that is produced. By way of example, on medical devices, it is typically important that the polymeric material adheres sufficiently to the surface of the medical device and does not peel or flake off. Therefore, a need exists for a deposition method that enhances adherence of the polymeric materials to the surface of the substrate.

SUMMARY OF THE INVENTION

The present application relates to a method for vapor depositing a polymeric coating onto a substrate. In an embodiment, the invention is a method for applying a polymer coating to a substrate comprising performing a bake-out cycle with a chemical vapor deposition system and performing a deposition cycle with the chemical vapor deposition system. The bake-out cycle can comprise creating a vacuum, heating an activation chamber, vaporizing residual parylene, and allowing vaporized residue to condense in a deposition chamber or a cold trap.

The above summary of the present invention is not intended to describe each discussed embodiment of the present invention. This is the purpose of the figures and the detailed description that follows.

DRAWINGS

The invention may be more completely understood in connection with the following drawings, in which.

Figure 5A:
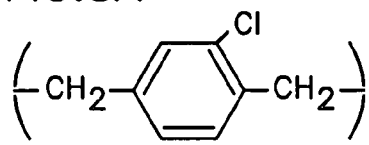
Figure 5B:
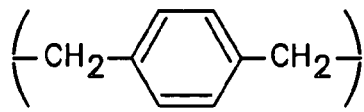
Figure 5C:
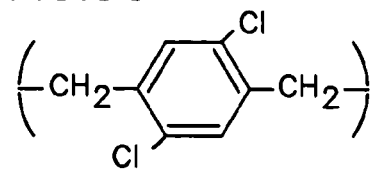

FIG. 5a shows the repeating subunit of parylene-C.
FIG. 5b shows the repeating subunit of parylene-N.
FIG. 5c shows the repeating subunit of parylene-D.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

In some applications, sufficient adhesion of a polymer to the surface of the substrate can be achieved simply through the formation of a cohesive layer that surrounds the substrate. In other applications, the polymeric materials must chemically bond with the surface of the substrate in order to provide sufficient adhesion. The present invention relates to methods for depositing a polymer on a substrate in a manner that can enhance bonding of the polymeric materials to the surface of the substrate.

It has been discovered that oxygen or ozone can react with activated monomer and can result in the formation of non-reactive (or less-reactive) species that do not chemically bond to the surface of the substrate to which it is applied. For example, oxygen or ozone can react with activated parylene monomer to form non-reactive parylene species (contaminants) that, while indirectly capable of bonding with other parylene monomers, will no longer bond properly with the surface of a substrate.

For some applications, where the polymeric materials must covalently bond with the surface of the substrate in order to provide sufficient adhesion, the presence of non-reactive parylene monomer species during deposition can prevent the resulting layer of polymeric material from possessing sufficient adhesion to the surface of a substrate. Lack of sufficient adhesion can lead to product failure because of peeling or flaking of the polymer layer.

As an example, where a substrate is a metal, such as stainless steel, the substrate may be treated with a silanating agent that chemically bonds with the surface of the metal substrate and provides an exposed reactive group, such as a vinyl group, that can then be used to covalently link a polymer, such as parylene, to the surface of the substrate. However, non-reactive species, if deposited over the reactive group can prevent reactive species from forming a covalent bond with the reactive group by occluding it. In this manner, the non-reactive species can prevent the polymer layer from having sufficient adhesion to the substrate.

With other types of substrates, a suitable reactive group may already exist on the surface of a substrate, such that a separate agent is not needed to provide a means of chemically bonding a polymer, such as parylene, to the surface of the substrate. Alternatively, there may be a cladding around the substrate that has a suitable reactive group. However, non-reactive species can still prevent the polymer layer that is applied from having sufficient adhesion in these instances. This is because the non-reactive species can still occlude the pre-existing reactive group and prevent the reactive species from binding with the substrate or cladding.

The present invention provides methods that reduce the incidence or quantity of unreactive, or reduced reactivity, parylene monomer species that are formed during, or that remain after, deposition cycles. In an embodiment, the present invention is a method that includes a cooling step before breaking vacuum and opening a deposition machine in order to reduce the formation of unreactive monomer species. In an embodiment, the present invention is a method that includes performing a bake-out cycle, in between deposition cycles, in order to reduce the amount of unreactive monomer that is deposited during a deposition cycle.

Figure 1:
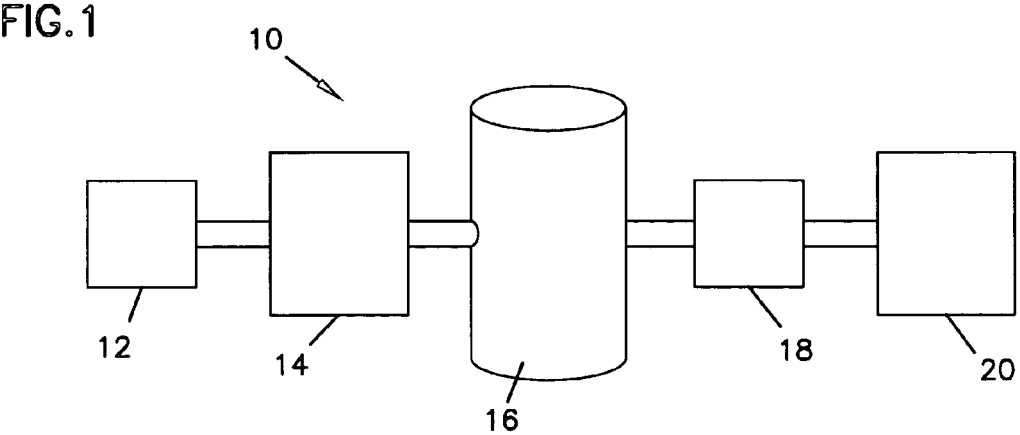
FIG. 1 is a schematic diagram of a chemical vapor deposition reactor system.

Referring now to FIG. 1, a schematic diagram of a chemical vapor deposition reactor system is shown. The system 10 comprises a vaporization chamber 12, a cracking chamber 14, a deposition chamber 16, a cold trap 18, and a vacuum pump 20. The vaporization chamber 12 is where a charge of parylene dimer is added before the deposition cycle is initiated. The amount of parylene to be deposited is controlled by the amount of parylene dimer that is added to the vaporization chamber 12 as a charge. The vaporization chamber 12 is in fluid communication with the cracking chamber 14. The cracking chamber 14 is where the vaporized parylene dimer, coming from the vaporization chamber 12, is then turned into an activated monomeric form. The cracking chamber is heated in order to turn the vaporized dimer into an activated monomer through a pyrolysis reaction. Specifically, the dimer is turned into a monomeric diradical by cleavage of the dimer at the two methylene-methylene bonds.

The cracking chamber 14 is in fluid communication with the deposition chamber 16. The deposition chamber 16 is where the activated monomer flows after the cracking chamber 14. The deposition chamber 16 is at a lower temperature than the cracking chamber and promotes the condensation of the activated monomer vapor. The deposition chamber 16 can have a door (not shown) to facilitate inserting and removing items to be coated. The deposition chamber 16 is in fluid communication with the cold trap 18. The cold trap 18 is where any residual vaporized parylene monomer or dimer that passes the deposition chamber 16 is trapped for later removal. The cold trap 18 prevents parylene monomer or dimer vapor from entering the vacuum pump 20. The cold trap 18 is in fluid communication with the vacuum pump 20. The vacuum pump 20 is attached to the deposition chamber and allows the process to take place under vacuum. The system can be sealed so that vacuum pressure (negative pressure) can be achieved and maintained. One of skill in the art will appreciate that chemical vapor deposition reactor systems may also comprise other components besides the basic components described here.

Figure 2:
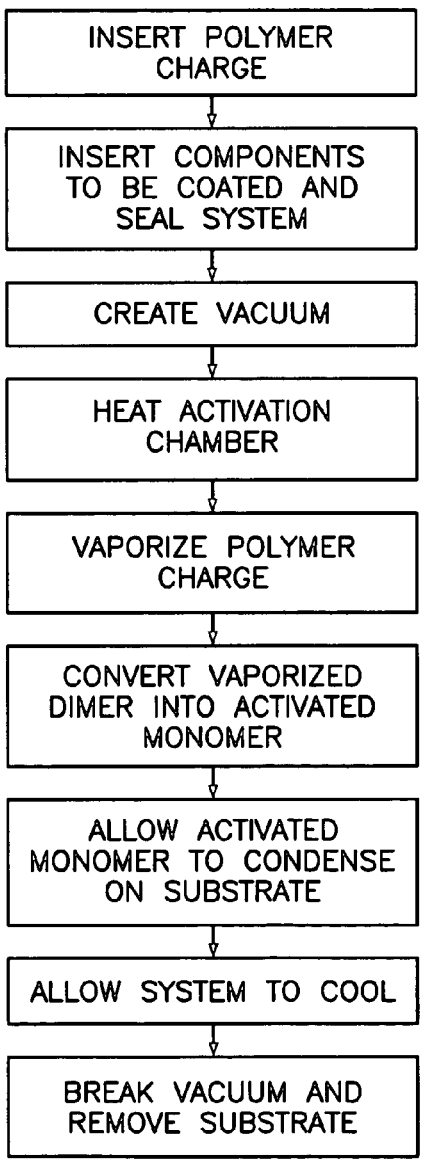
FIG. 2 is a flowchart showing operations performed in a deposition cycle of a chemical vapor deposition method.

Referring now to FIG. 2, a flowchart of an exemplary deposition cycle is shown. A polymer charge is inserted into the vaporization chamber 12. Components to be coated are then inserted into the deposition chamber 16. The system 10 is sealed and then the vacuum pump 20 is turned on to lower the pressure in the system 10 to below a certain pre-designated level. In an embodiment, the pressure of the system may be about 0.1 torr. However, one of skill in the art will appreciate that other pressures can be used. The cracking chamber 14 is then heated to a temperature sufficient to cause parylene dimer vapor to crack into activated monomer vapor. If the temperature is not high enough, the parylene dimer vapor may not all crack into activated monomer vapor. In an embodiment, the cracking chamber 14 is heated to at least 500 degrees Celsius. Heating the cracking chamber 14 more than is necessary may be economically inefficient. The cracking chamber 14 is heated to less than 1000 degrees Celsius in some embodiments. In a particular embodiment, the cracking chamber 14 is heated to between about 600 and about 900 degrees Celsius.

Once the cracking chamber 14 has reached the desired temperature, the vaporization chamber 12 is then heated to start producing vaporized parylene dimer. The amount of vaporized parylene dimer being created can be controlled by controlling the amount of heat in the vaporization chamber 12. If not enough heat is supplied to the vaporization chamber 12, the parylene will not vaporize. In an embodiment, the vaporization chamber is heated to greater than about 80 degrees Celsius. Applying more heat than is necessary may cause vaporization to occur too rapidly. In an embodiment, the vaporization chamber is heated to less than about 200 degrees Celsius. As an example, the vaporization chamber maybe heated to a level of between about 100 and about 160 degrees Celsius.

As the vacuum pump 20 creates a negative pressure, vaporized components are drawn from the vaporization chamber 12, through the cracking chamber 14, and into the deposition chamber 16. Specifically, vaporized parylene dimer is drawn from the vaporization chamber 12, into the heated cracking chamber 14, where vaporized dimer is turned into a vaporized activated monomer form through a pyrolytic reaction. The vaporized activated monomer then drawn from the heated cracking chamber 14 into the deposition chamber 16. The deposition chamber 16 is typically cooler than the heated cracking chamber 14. If the deposition chamber is not sufficiently cool, the activated monomer will not condense properly onto the substrate. In an embodiment, the temperature of the deposition chamber 16 is less than about 80 degrees Celsius. If the deposition chamber is too cold, the activated monomer will condense too rapidly onto the substrate. In an embodiment, the temperature of the deposition chamber is greater than about 0 degrees Celsius. In an exemplary method, the temperature of the deposition chamber 16 is between about 20 and about 25 degrees Celsius. In a particular embodiment the temperature of the deposition chamber 16 is about room temperature. The activated monomer can react with other monomer molecules as well as the surface of the substrate, depending on the chemical composition of the particular substrate surface and the particular monomer being used.

Vaporized components that do not condense in the deposition chamber 16 are then drawn into the cold trap 18. The cold trap 18 is cooled to ensure that substantially all vaporized polymer components that enter the cold trap 18 are deposited there and do not enter the vacuum pump 20. In an embodiment, the cold trap is cooled to about −80 degrees Celsius.

After the desired amount of parylene dimer has passed from the vaporization chamber 12, through the heated cracking chamber 14, and into the deposition chamber 16, heat is generally no longer applied to the vaporization chamber 12 and the heated cracking chamber 14, causing the system to gradually cool down. After the system has cooled down below a desired level, the vacuum is shut-off and the system can then opened up to remove the now coated substrate that is in the deposition chamber. If the system has not cooled down sufficiently before opening up the system, it is believed that activated monomer vapor that may be left in the system can more easily react with oxygen or ozone from the environment and result in the formation of a non-reactive parylene monomer species. Therefore, in an embodiment, the system is cooled to below about 300 degrees Celsius before breaking vacuum and opening up the system. In an embodiment, the system is cooled to below about 200 degrees Celsius. In a particular embodiment, the system is cooled to between about 300 degrees Celsius and about 20 degrees Celsius before breaking vacuum and opening up the system. While FIG. 2 shows a sequence of steps taken in an exemplary deposition cycle, one of skill in the art will appreciate that the sequence of performing the steps can be varied while remaining within the scope of the present invention.

Figure 3:
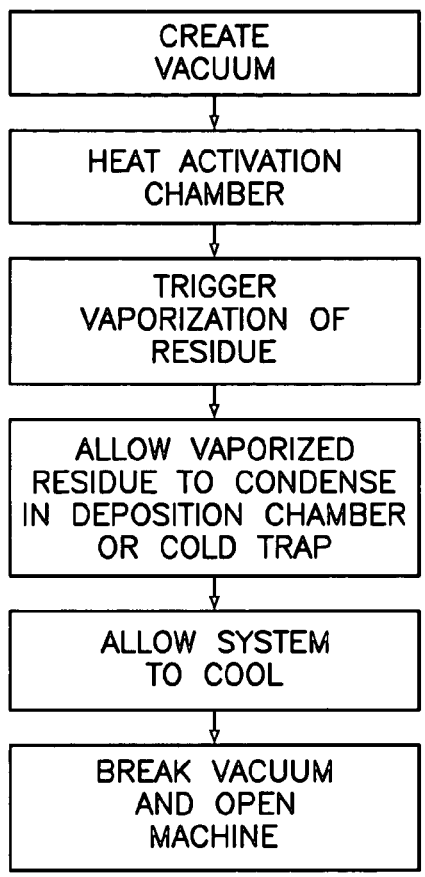
FIG. 3 is a flowchart showing operations performed in a bake-out cycle of a chemical vapor deposition method.

Referring now to FIG. 3, a flowchart of an exemplary bake-out cycle is shown. The system 10 is sealed and then the vacuum pump 20 is turned on to lower the pressure in the system 10 to below a certain pre-designated level. The cracking chamber 14 can then be heated to the same levels as during the deposition cycle. In an embodiment, the cracking chamber 14 is heated to at least 500 degrees Celsius. In an embodiment, the cracking chamber 14 is heated to less than 1000 degrees Celsius. In a particular embodiment, the cracking chamber 14 is heated to between about 600 and about 900 degrees Celsius. Once the cracking chamber 14 has reached the desired temperature, the vaporization chamber 12 is then heated. While a charge of parylene dimer is not added to the vaporization chamber 12 before the start of the bake-out cycle, the vaporization chamber 12 is still heated so that any residual parylene dimer and/or monomer that may be present is vaporized. In an embodiment, the vaporization chamber is heated to greater than about 80 degrees Celsius. In an embodiment, the vaporization chamber is heated to less than about 200 degrees Celsius. In an embodiment, the vaporization chamber maybe heated to a level of between 100 and 160 degrees Celsius.

The residual vaporized parylene monomer and/or dimer is then drawn through the system into the heated cracking chamber 14 where vaporized dimer is turned into a vaporized activated monomer form through a pyrolytic reaction. However, it is believed that the non-reactive species will not be converted back into an activated monomer form. The residual vaporized monomer (both activated and non-reactive) and/or dimer then passes into the deposition chamber 16 that is cooler than the heated cracking chamber 14. In an embodiment, the temperature of the deposition chamber 16 is less than about 80 degrees Celsius. In an embodiment, the temperature of the deposition chamber is greater than about 0 degrees Celsius. In an embodiment, the temperature of the deposition chamber 16 is between about 20 and about 25 degrees Celsius. In a particular embodiment the temperature of the deposition chamber 16 is about room temperature during the bake-out cycle. The vaporized monomer and/or dimer condenses at the cooler temperature of the deposition chamber 16. By way of example, some of the residual vaporized monomer and/or dimer condenses onto the surfaces inside the deposition chamber. After the cycle is over, the condensed monomer and/or dimer may be cleaned out of the deposition chamber. Some of the residual vaporized activated monomer and/or dimer may also pass through the deposition chamber into the cold trap 20. After the cycle is over, the condensed monomer and/or dimer may be cleaned out of the cold trap. In this manner, non-reactive species may be removed from the vapor deposition system so that they are reduced, or no longer present, so as to not interfere with deposition cycles.

After a period of time sufficient for residual parylene monomer and/or dimer to pass from the vaporization chamber 12, through the heated cracking chamber 14, into the deposition chamber 16, and into the cold trap 20, heat is no longer applied to the heated cracking chamber 14 or the vaporization chamber 12, causing the system to gradually cool down. After the system has cooled down below a desired level, the vacuum is shut-off and the system is then opened up. In an embodiment, the system is cooled to below about 300 degrees Celsius before breaking vacuum and opening up the system. In an embodiment, the system is cooled to below about 200 degrees Celsius. In a particular embodiment, the system is cooled to between about 300 degrees Celsius and about 20 degrees Celsius before breaking vacuum and opening up the system. It is believed that performing a bake-out cycle reduces the amount of non-reactive parylene monomer that is present as a contaminant during a deposition cycle. The parylene chemical vapor deposition (CVD) reactor system is now ready for another deposition cycle. While FIG. 3 shows a sequence of steps taken in an exemplary bake-out cycle, one of skill in the art will appreciate that the sequence of performing the steps can be varied while remaining within the scope of the present invention.

Figure 4:
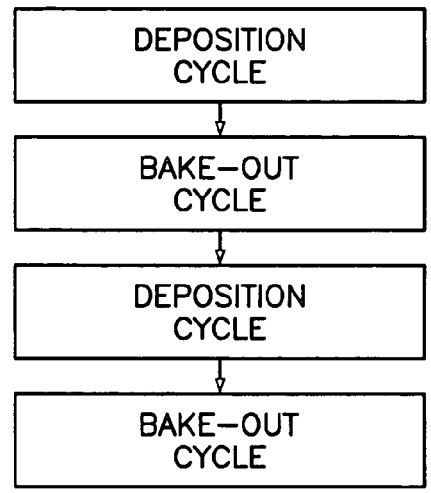
FIG. 4 is a flowchart showing alternation of deposition cycles and bake-out cycles.

Referring now to FIG. 4, a flowchart is provided showing alternation of deposition cycles and bake-out cycles. In commercial production applications, components may be coated with a polymer in a deposition chamber serially in lots. For example, a parylene coating may be applied to a given lot of devices in a batch process. Where a chemical vapor deposition system is clean and reasonably devoid of contaminants initially, a deposition cycle can be performed first. Following the deposition cycle, a bake-out cycle can be performed to reduce the amount of non-reactive parylene monomer that is present as a possible contaminant. Then, another deposition cycle can be performed after the bake-out cycle. The deposition cycle and the bake-out cycles can be alternated, serially, during production. Where the status of a given chemical vapor deposition system is unknown, a bake-out cycle can be performed first followed by a deposition cycle and then alternating between bake-out cycles and deposition cycles. It is believed that the amount of non-reactive parylene monomer that is present as a contaminant during a deposition cycle can be reduced using varying cycle sequences. In an embodiment, numerous deposition cycles can be performed before contaminants are removed in a bake-out cycle. However, in a particular embodiment, a bake-out cycle follows every deposition cycle.

Substrates

Methods of the invention can be used to apply a polymer coating onto a variety of substrate surfaces including metals, polymers, ceramics, and natural materials.

Metals include, but are not limited to, titanium, stainless steel, and cobalt chromium. Suitable metals can also include the noble metals such as gold, silver, copper, and platinum. Finally, suitable metals can include alloys such as nitinol or cobalt chromium alloys.

Polymers include those formed of synthetic polymers, including oligomers, homopolymers, and copolymers resulting from either addition or condensation polymerizations. Examples include, but not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; vinyls such as ethylene, propylene, styrene, vinyl chloride, vinyl acetate, vinyl pyrrolidone, and vinylidene difluoride, condensation polymers including, but are not limited to, nylons such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polylactic acid, polyglycolic acid, polydimethylsiloxanes, and polyetheretherketone.

Ceramics include, but are not limited to, silicon nitride, silicon carbide, zirconia, and alumina, as well as glass, silica, and sapphire.

Certain natural materials are also suitable including human tissue, when used as a component of a device, such as bone, cartilage, skin and teeth; and other organic materials such as wood, cellulose, compressed carbon, rubber, silk, wool, and cotton. The composition of the substrate can also include resins, polysaccharides, silicon, or silica-based materials, glass, films, gels, and membranes.

Treatment of Substrates

Some substrates may be treated to enhance bonding before a polymer layer is applied in accordance with an embodiment of the invention. By way of example, a substrate may be treated with a silanating agent to promote adhesion of the parylene polymer coating. The silanating agent would operate to modify the surface of the substrate prior to deposition of a polymer coating, such as a parylene coating. Suitable silanating agents can include 3-acryloxypropyltrichlorosilane, 3-acryloxypropyltrimethoxysilane, allyltrichlorosilane, allyltriethoxysilane, allyltrimethoxysilane, 4-butenyltrichlorosilane, 6-hex-1-enyltrichlorosilane, (methacryloxymethyl)triethoxysilane, (methacryloxymethyl)trimethoxysilane, 3-methacryloxypropyltrichlorosilane, 3-methacryloxypropyltrimethoxysilane, 3-methacryloxypropyltriethoxysilane, 1,7-octadienyltriethoxysilane, 7-oct-1-enyltrichlorosilane, 7-oct-1-enyltrimethoxysilane, vinyltrichlorosilane, vinyltrimethoxysilane, vinyltriethoxysilane, vinyltriacetoxysilane, and the like. One of skill in the art will appreciate that other silanating agents that contain vinyl, acryl, or methacryl can also be used. In an embodiment, the silanating agent is 3-methacryloxypropyltrimethoxysilane.

In some embodiments, the substrate surface may be chlorinated prior to application of the polymer coating for generating an increased polar surface that can operate to yield a stronger molecular bond with the polymer coating applied thereon.

In an embodiment of the invention, a substrate is cleaned before application of a vapor deposited polymer. One of skill in the art will appreciate that a substrate can be cleaned in many different manners including frictional cleaning, use of detergents, use of degreasing agents, etc.

Polymers Deposited

"Parylene" is both a generic name for a known group of polymers based on p-xylylene and made by vapor or plasma phase polymerization, and a name for the unsubstituted form of the polymer. By way of example, an unsubstituted parylene polymer can have the repeating structure -(p-CH$_2$—C$_6$H$_4$—CH$_2$)$_n$—, with n equal to about 5,000 daltons, and a molecular weight of about 500,000 daltons. The term "parylene derivative" will refer to the known group of polymers based on p-xylylene and made by vapor or plasma phase polymerization. Common parylene derivatives include parylene-C (see FIG. 5a), parylene-N (see FIG. 5b), and parylene-D (see FIG. 5c).

In an embodiment, the polymer deposited by the method includes at least one of poly 2-chloro-paraxylylene (parylene C), polyparaxylylene (parylene N), poly 2,5-dichloro-paraxylylene (parylene D). In some embodiments, the polymer deposited by the method includes poly 2-chloro-paraxylylene (parylene C). In some embodiments, the polymer deposited by the method includes poly 2,3,5,6-tetrafluoro-paraxylylene.

In an embodiment, the polymer deposited by the method includes mono-, di-, tri-, and tetra-halo substituted polyparaxylylene. In an embodiment, the polymer includes mono-, di-, tri-, and tetra-chloro substituted polyparaxylylene. In an embodiment, the polymer includes mono-, di-, tri-, and tetra-fluoro substituted polyparaxylylene. Other parylene derivatives may include poly(dimethoxy-p-xylylene), poly(sulfo-p-xylylene), poly(iodo-p-xylylene), poly(trifluoro-p-xylylene), poly(difluoro-p-xylylene), and poly(fluoro-p-xylylene).

Parylene and parylene derivative coatings applicable by vapor deposition are commercially available from or through a variety of sources, including Specialty Coating Systems (100 Deposition Drive, Clear Lake, Wis. 54005), Para Tech Coating, Inc. (35 Argonaut, Aliso Viejo, Calif. 92656) and Advanced Surface Technology, Inc. (9 Linnel Circle, Billerica, Mass. 01821-3902).

However, one of skill in the art will appreciate that methods of the invention can also be used with other vapor deposited polymers and copolymers of vapor deposited polymers. For example, other vapor deposited polymers include, poly(p-phenylene-vinylene), polyimides, and phenylmaleimide.

Devices

In some embodiments of the invention, the substrate onto which a polymer is deposited may be part of a medical device. These devices can include both implantable devices and non-implantable medical devices.

Embodiments of the invention can be used with implantable, or transitorily implantable, devices including, but not limited to, vascular devices such as grafts (e.g., abdominal aortic aneurysm grafts, etc.), stents (e.g., self-expanding stents typically made from nitinol, balloon-expanded stents typically prepared from stainless steel, degradable coronary stents, etc.), catheters (including arterial, intravenous, blood pressure, stent graft, etc.), valves (e.g., polymeric or carbon mechanical valves, tissue valves, valve designs including percutaneous, sewing cuff, and the like), embolic protection filters (including distal protection devices), vena cava filters, aneurysm exclusion devices, artificial hearts, cardiac jackets, and heart assist devices (including left ventricle assist devices), implantable defibrillators, electro-stimulation devices and leads (including pacemakers, lead adapters and lead connectors), implanted medical device power supplies (e.g., batteries, etc.), peripheral cardiovascular devices, atrial septal defect closures, left atrial appendage filters, valve annuloplasty devices (e.g., annuloplasty rings), mitral valve repair devices, vascular intervention devices, ventricular assist pumps, and vascular access devices (including parenteral feeding catheters, vascular access ports, central venous access catheters); surgical devices such as sutures of all types, staples, anastomosis devices (including anastomotic closures), suture anchors, hemostatic barriers, screws, plates, clips, vascular implants, tissue scaffolds, cerebro-spinal fluid shunts, shunts for hydrocephalus, drainage tubes, catheters including thoracic cavity suction drainage catheters, abscess drainage catheters, biliary drainage products, and implantable pumps; orthopedic devices such as joint implants, acetabular cups, patellar buttons, bone repair/augmentation devices, spinal devices (e.g., vertebral disks and the like), bone pins, cartilage repair devices, and artificial tendons; dental devices such as dental implants and dental fracture repair devices; drug delivery devices such as drug delivery pumps, implanted drug infusion tubes, drug infusion catheters, and intravitreal drug delivery devices; ophthalmic devices including orbital implants, glaucoma drain shunts and intraocular lenses; urological devices such as penile devices (e.g., impotence implants), sphincter, urethral, prostate, and bladder devices (e.g., incontinence devices, benign prostate hyperplasia management devices, prostate cancer implants, etc.), urinary catheters including indwelling ("Foley") and non-indwelling urinary catheters, and renal devices; synthetic prostheses such as breast prostheses and artificial organs (e.g., pancreas, liver, lungs, heart, etc.); respiratory devices including lung catheters; neurological devices such as neurostimulators, neurological catheters, neurovascular balloon catheters, neuro-aneurysm treatment coils, and neuropatches; ear nose and throat devices such as nasal buttons, nasal and airway splints, nasal tampons, ear wicks, ear drainage tubes, tympanostomy vent tubes, otological strips, laryngectomy tubes, esophageal tubes, esophageal stents, laryngeal stents, salivary bypass tubes, and tracheostomy tubes; biosensor devices including glucose sensors, cardiac sensors, intra-arterial blood gas sensors; oncological implants; and pain management implants.

Classes of suitable non-implantable devices can include dialysis devices and associated tubing, catheters, membranes, and grafts; autotransfusion devices; vascular and surgical devices including atherectomy catheters, angiographic catheters, intraaortic balloon pumps, intracardiac suction devices, blood pumps, blood oxygenator devices (including tubing and membranes), blood filters, blood temperature monitors, hemoperfusion units, plasmapheresis units, transition sheaths, dialators, intrauterine pressure devices, clot extraction catheters, percutaneous transluminal angioplasty catheters, electrophysiology catheters, breathing circuit connectors, stylets (vascular and non-vascular), coronary guide wires, peripheral guide wires; dialators (e.g., urinary, etc.); surgical instruments (e.g. scalpels and the like); endoscopic devices (such as endoscopic surgical tissue extractors, esophageal stethoscopes); and general medical and medically related devices including blood storage bags, umbilical tape, membranes, gloves, surgical drapes, wound dressings, wound management devices, needles, percutaneous closure devices, transducer protectors, pessary, uterine bleeding patches, PAP brushes, clamps (including bulldog clamps), cannulae, cell culture devices, materials for in vitro diagnostics, chromatographic support materials, infection control devices, colostomy bag attachment devices, birth control devices; disposable temperature probes; and pledgets.

One of skill in the art will appreciate that methods of the invention can also be used to deposit polymers onto devices other than medical devices.

While the present invention has been described with reference to several particular implementations, those skilled in the art will recognize that many changes may be made hereto without departing from the spirit and scope of the present invention.

I claim:

1. A method for applying a polymer coating to a substrate comprising:
   performing a bake-out cycle with a multi-chambered chemical vapor deposition system, the multi-chambered chemical vapor deposition system comprising a vaporization chamber, a cracking chamber, and a deposition chamber, the bake-out cycle comprising heating the vaporization and/or cracking chamber to a temperature adequate to vaporize any residual contaminants while maintaining the deposition chamber at a temperature of less than 80 degrees Celsius, and removing the contaminants, and
   performing a deposition cycle with the chemical vapor deposition system, the deposition cycle comprising depositing a polymer onto the substrate.

2. The method of claim 1, wherein performing the bake-out cycle comprises heating the cracking chamber to at least 600 degrees Celsius.

3. The method of claim 1, wherein performing the bake-out cycle comprises heating the vaporization chamber to at least 80 degrees Celsius.

4. The method of claim 2, wherein performing the bake-out cycle comprises cooling the cracking chamber to at least 300 degrees Celsius.

5. The method of claim 1, wherein performing the deposition cycle comprises adding a charge of a polymer dimer to the vaporization chamber.

6. The method of claim 1, wherein performing the deposition cycle comprises heating the cracking chamber to at least 600 degrees Celsius.

7. The method of claim 1, wherein performing the deposition cycle comprises heating the vaporization chamber to at least 80 degrees Celsius.

8. The method of claim 1, wherein performing the deposition cycle comprises condensing a monomer vapor onto the substrate.

9. The method of claim 1, the substrate comprising stainless steel.

10. The method of claim 1, wherein performing the deposition cycle further comprises cooling the cracking chamber to at least 300 degrees Celsius.

11. The method of claim 1, the polymer comprising at least one of poly 2-chloro-paraxylylene (parylene C), polyparaxylylene (parylene N), poly 2,5-dichloro-paraxylylene (parylene D).

12. The method of claim 1, the polymer comprising poly 2-chloro-paraxylylene (parylene C).

13. The method of claim 1, wherein the step of performing a deposition cycle with a chemical vapor deposition system is performed after the step of performing a bake-out cycle with the chemical vapor deposition system.

14. The method of claim 1, wherein the step of performing a bake-out cycle with the chemical vapor deposition system is performed after the step of performing a deposition cycle with a chemical vapor deposition system.

15. The method of claim 1, wherein the step of performing a deposition cycle is alternated with the step of performing a bake-out cycle.

16. The method of claim 1, the substrate comprising a medical device.

17. The method of claim 16, the medical device comprising a stent.

18. A method of using a chemical vapor deposition system to coat a substrate with a polymer, comprising performing a coating cycle and performing a cleaning cycle, the cleaning cycle comprising heating a vaporization and/or cracking chamber of the chemical vapor deposition system while keeping a deposition chamber of the chemical vapor deposition system at a temperature of less than 80 degrees Celsius, the coating cycle comprising condensing a monomer vapor onto the substrate and opening the system, wherein the system is opened prior to initiating the cleaning cycle.

19. The method of claim 18, wherein the cleaning cycle comprises removing non-reactive monomer from the chemical vapor deposition system.

20. The method of claim 18, the polymer comprising parylene.

21. The method of claim 18, wherein the coating cycle comprises heating the cracking chamber to at least 600 degrees Celsius.

22. The method of claim 18, wherein the coating cycle comprises heating a vaporization chamber to at least 80 degrees Celsius.

23. The method of claim 18, the monomer vapor comprising monomeric diradicals of parylene.

24. The method of claim 18, the substrate comprising stainless steel.

25. The method of claim 18, wherein the coating cycle comprises cooling the cracking chamber to less than 300 degrees Celsius.

26. The method of claim 18, wherein the cleaning cycle comprises heating the cracking chamber to at least 600 degrees Celsius.

27. The method of claim 18, wherein the cleaning cycle comprises heating the vaporization chamber to at least 80 degrees Celsius.

28. The method of claim 18, wherein the cleaning cycle comprises cooling the cracking chamber to less than 300 degrees Celsius.

29. The method of claim 18, wherein the cleaning cycle is performed after the coating cycle.

30. The method of claim 18, wherein the coating cycle is performed after the cleaning cycle.

31. The method of claim 18, wherein a cleaning cycle follows every coating cycle.

* * * * *

UNITED STATES PATENT AND TRADEMARK OFFICE
CERTIFICATE OF CORRECTION

PATENT NO. : 7,575,781 B2  Page 1 of 1
APPLICATION NO. : 10/911228
DATED : August 18, 2009
INVENTOR(S) : Ralph A. Chappa It is certified that error appears in the above-identified patent and that said Letters Patent is hereby corrected as shown below:

Front Page, (73) Assignee: "Sur Modics, Inc." should read --SurModics, Inc.--

Signed and Sealed this

Fifth Day of January, 2010

David J. Kappos
*Director of the United States Patent and Trademark Office*

UNITED STATES PATENT AND TRADEMARK OFFICE
CERTIFICATE OF CORRECTION

PATENT NO.        : 7,575,781 B2                                           Page 1 of 1
APPLICATION NO.   : 10/911228
DATED             : August 18, 2009
INVENTOR(S)       : Ralph A. Chappa It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 781 days.

Signed and Sealed this

Seventh Day of September, 2010

David J. Kappos
*Director of the United States Patent and Trademark Office*